United States Patent [19]

Goodsir et al.

[11] Patent Number: 5,242,423
[45] Date of Patent: Sep. 7, 1993

[54] NEEDLELESS SYRINGE

[75] Inventors: Stephen W. Goodsir, Wayne; Paul Y. McCormick, Chester Springs; Dale C. Steiner, Akron, all of Pa.

[73] Assignee: American Home Products Corporation, New York, N.Y.

[21] Appl. No.: 848,481

[22] Filed: Mar. 9, 1992

[51] Int. Cl.$^5$ ............................................. A61M 5/00
[52] U.S. Cl. ............................ 604/243; 604/905; 604/283
[58] Field of Search .............. 604/905, 246–249, 604/30–34, 200–205, 280, 283

[56] References Cited

U.S. PATENT DOCUMENTS

| | | | |
|---|---|---|---|
| 4,143,853 | 3/1979 | Abramson | 604/246 |
| 4,210,173 | 7/1980 | Choksi et al. | 604/246 |
| 4,387,879 | 6/1983 | Tauchinski | 604/247 |
| 4,683,916 | 8/1987 | Raines . | |
| 4,842,591 | 6/1989 | Cutner | 604/905 |
| 4,898,581 | 2/1990 | Iwatschenko | 604/247 |
| 4,915,687 | 4/1990 | Sivert . | |
| 5,062,836 | 11/1991 | Wendell | 604/249 |
| 5,071,413 | 12/1991 | Utterberg | 604/905 |
| 5,137,527 | 8/1992 | Miller et al. | 604/905 |

Primary Examiner—John D. Yasko
Assistant Examiner—Chalin Smith
Attorney, Agent, or Firm—Richard K. Jackson

[57] ABSTRACT

A needleless syringe comprising a barrel, a plunger and a truncated cannula secured to said barrel by an externally stepped hub connector comprising (1) a tubular skirt section of greatest circumference secured to the constricted distal end of said barrel through which said fluid transfer tube extends; (2) a tubular male tapered section of smaller circumference situated beyond the constricted distal end of said barrel and through which said fluid transfer tube extends; and (3) a tubular forward extension of smallest circumference into which said fluid transfer tube projects to a point near the discharge aperture of said forward extension, said forward extension having an annular projection about its circumference set forward of said tapered section a distance sufficient to create a seal between said tapered section and a female Luer slip fitting of a valve actuated intravenous port device when said annular projection opens said valve, said annular projection having a circumference smaller than the smallest circumference of said tapered section. The discharge aperture of said forward extension is blunt and of sufficient diameter to minimize any chance of puncturing the user's or patient's skin.

5 Claims, 2 Drawing Sheets

NEEDLELESS SYRINGE

BACKGROUND OF THE INVENTION

The problem of accidental needle sticks by medical personnel while working with conventional hypodermic syringes has become more acute with the increase in the seriousness of blood transmittable diseases such as Acquired Immune Deficiency Syndrome. The development of complex shielding devices to cover hypodermic syringe needles has met with some success although the more complex devices involved require additional education in their use and in some instances require manipulation which in itself can lead to sticking accidents because of the user's unfamiliarity with the pulling or twisting motions required to sheath or unsheath the needle.

Parental drug administration is very frequently carried out by introducing the drug intravenously through an indwelling cannula which is attached externally via tubing, to a bottle or flexible bag of intravenous solution. Where two intravenous solutions are to be simultaneously infused, the tubing is made-up with Y-sites which afford a second site for connection with the second intravenous solution, whether that second solution be a syringe, bottle, or flexible bag. When a syringe is used to introduce a bolus medicament through a Y-site, conventionally the needle of the syringe is passed through a flexible rubber diaphragm cover of the Y-site and the plunger of the syringe is activated to force the liquid medicament into the tubing line where it passes into the patient through the indwelling cannula. With the development of new Y-site port systems such as the Safsite ® reflux valve (RV-1000) and check valve (BC-1000) developed by Burron Medical Inc. and the Interlink ® IV Access System of Baxter Healthcare Corp., needleless syringes have become practical.

DESCRIPTION OF THE INVENTION

In accordance with this invention, there is provided a needleless syringe comprising a barrel consisting of a tube with a constricted distal end region, a plunger disposed within the barrel and a fluid transfer tube extending into and secured to the constricted distal end of said barrel by an externally stepped hub through which said fluid transfer tube partially extends, said externally stepped hub connector comprising (1) a tubular skirt section of greatest circumference secured to the constricted distal end of said barrel through which said fluid transfer tube extends; (2) a tubular male tapered section of smaller circumference situated beyond the constricted distal end of said barrel and through which said fluid transfer tube extends; and (3) a tubular forward extension of smallest circumference into which said fluid transfer tube projects to a point near the discharge aperture of said forward extension, said forward extension having an annular projection about its circumference set forward of said tapered section a distance sufficient to create a seal between said tapered section and a female Luer slip fitting of a valve-actuated intravenous port device when said annular projection on said forward extension opens said valve, said annular projection having a circumference smaller than the smallest circumference of said tapered section. The discharge aperture of said forward extension is blunt and of sufficient diameter to minimize any chance of puncturing the user's or patient's skin.

After sterilization of the needleless syringe, the forward extension and circumferential ring, up to and including the modified Luer slip, are kept covered to maintain sterility of these critical parts during storage prior to use. The cover employed is made of rubber or its equivalent as with conventional cannula covers but is fitted for the hub connector of this invention to form a seal at the discharge aperture of the forward extension and at the tapered section of the hub connector.

The tapered section of the hub connector is a modified Luer taper fitting larger than a standard Luer slip at its connection to the tubular skirt section of the hub connector and smaller than the largest diameter of a standard Luer slip at its connection to the forward tubular extension. Hence, the tapered section of the hub connector will fit into a standard female Luer slip fitting, forming a liquid-air tight connection without perfect mating as with a standard Luer slip. The modified Luer slip fitting is easily separated for withdrawal and disposal after use of the needleless syringe of this invention.

The needleless syringe of this invention is used to transfer intravenous compatible fluids containing a medicament via a needleless injection port arrangement indwelling in a patient in need of intravenous administration of medication. The single-use throw away syringe avoids any conceivable post-use manipulation that could transfer infection from a patient to the medical personnel administering the intravenous solution and reduces problems of maintaining asepsis. Of course, the needleless syringe of this invention may be used repeatedly in such applications as admixing of intravenous solution ingredients in a vial or intravenous bag equipped with a needleless port device. When used in conjunction with injection port valved systems such as are disclosed in U.S. Pat. Nos. 4,683,916 and 4,915,687, the circumferential ring on the forward extension of the hub connector serves to contact the movable valve head element which with pressure slides inward in the female part of the injection port assembly thereby engaging and opening the valve at which point the modified Luer slip section of the hub connector seals the female Luer slip of the injection port system. Operation of the plunger in the barrel of the hyperdermic syringe of this invention forces medicament containing intravenous fluid through the check valve which upon removal of the syringe reseats itself to maintain an aseptic condition. In other applications, the syringe of this invention can be hooked up directly with any female Luer connection common with intravenous delivery systems and intravenous blood collection tube adapters. Normally the female Luer connection of the Y-site of the indwelling cannula tubing will be replaced or capped after each use of the needleless syringe of this invention to maintain asepsis. In addition to its use with the check valve port systems, the forward extension of the hub connector of the syringe of this invention can be inserted directly through slit diaphragm port injection devices used in Y-sites of other intravenous cannula systems, where once in place the circumferential ring serves to help hold the tip of the forward extension of the stepped hub connector in these types of ports while injection is given.

BRIEF DESCRIPTION OF THE DRAWINGS

FIG. 2 illustrates the closed valve mode while FIG. 3 illustrates the open valve mode of the intravenous port.

DETAILED DESCRIPTION OF THE INVENTION

Figure 1:
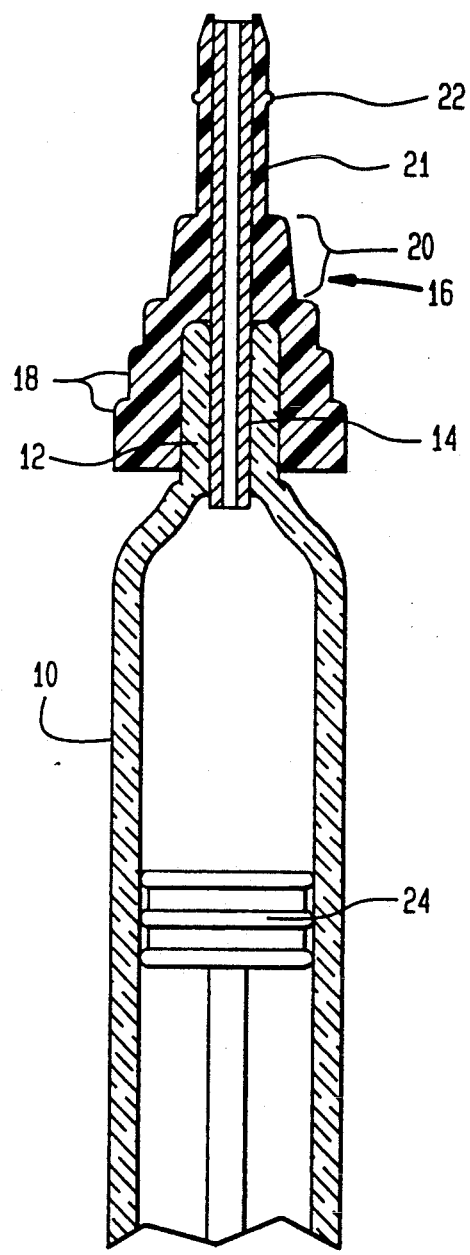
FIG. 1 is a cross-section of the needleless syringe of this invention.

With reference to the drawing FIG. 1, the present invention will be seen to comprise a needleless syringe generally designated 1 which is constructed from a glass or plastic barrel 10 which is constricted at its distal end 12, a plunger 24 disposed within the region of largest diameter of the barrel and a fluid transfer tube 14 constructed from rigid plastic or preferably metal (stainless steel). The fluid transfer tube 14 is secured to the constricted distal end of the barrel by an externally stepped hub connector 16 which is formed from any suitable plastic material such as nylon, which is most desirable. It must be understood that the plastic material from which the hub connector is formed has sufficient resilience to reform its original configuration if it is forcibly distorted or displaced. Hub connector 16 comprises three step regions of varying diameters. The skirt region 18 serves to secure the fluid transfer tube 14 to the constricted distal end 12 of the barrel 10. The tapered section 20 of smaller diameter than the skirt section 18 forms a modified Luer stub which at its largest diameter is larger than the greatest standard Luer dimension (0.170 inch) and at its smallest diameter is smaller than the greatest standard Luer dimension while presenting a taper which will partially fill a female Luer slip fitting. For example, the taper region of the hub connector of this invention is from about 0.172 to about 0.180 inches in diameter at its large end and from about 0.167 to about 0.159 inches at its smallest end over a length of from about 0.250 to about 0.120 inches. Preferably, the taper runs from about 0.175 to about 0.165 inches through an approximate 0.130 inch length. And, the narrow nose or post section 21 which is forward extension of said hub connector 16, and of smaller diameter than said modified Luer slip fitting 20 and which bears an annular projection 22 about its circumference located at a position such that the ring 22 bears upon and opens valve opening means within an injection port valve system, and the modified Luer slip fitting simultaneously completes a seal within the female Luer slip fitting of the intravenous injection port. The operation is best shown in FIG. 3, in conjunction with the check valve assembly of U.S. Pat. No. 4,683,916, the disclosure of which is incorporated herein by reference to show the valve that FIGS. 2 and 3 depict in operation with the needleless syringe of this invention.

Where the modified Luer stub projects from about 0.125 to about 0.135 and preferably about 0.130 inches from the skirt section, the annular projection 22 is located about 0.320 to about 0.210 inches, and preferably about 0.187 inches, forward of the Luer tapered region.

Figure 2:
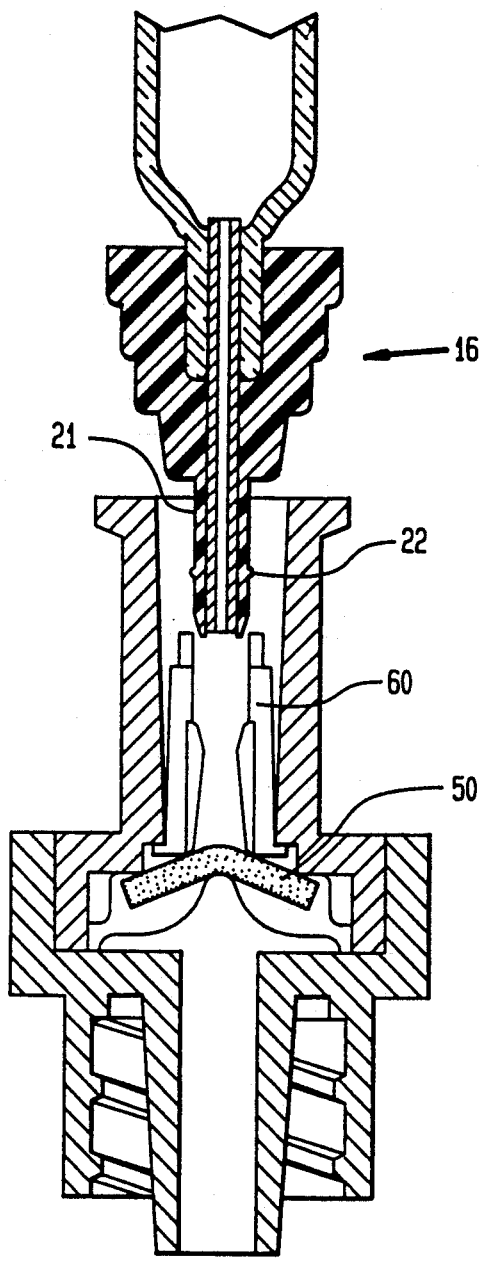
FIGS. 2 and 3 depict in cross-section, the mechanical operation of a check valve in an injection port suitable for use with an indwelling intravenous catheter when using the needleless syringe of this invention.
Figure 3:
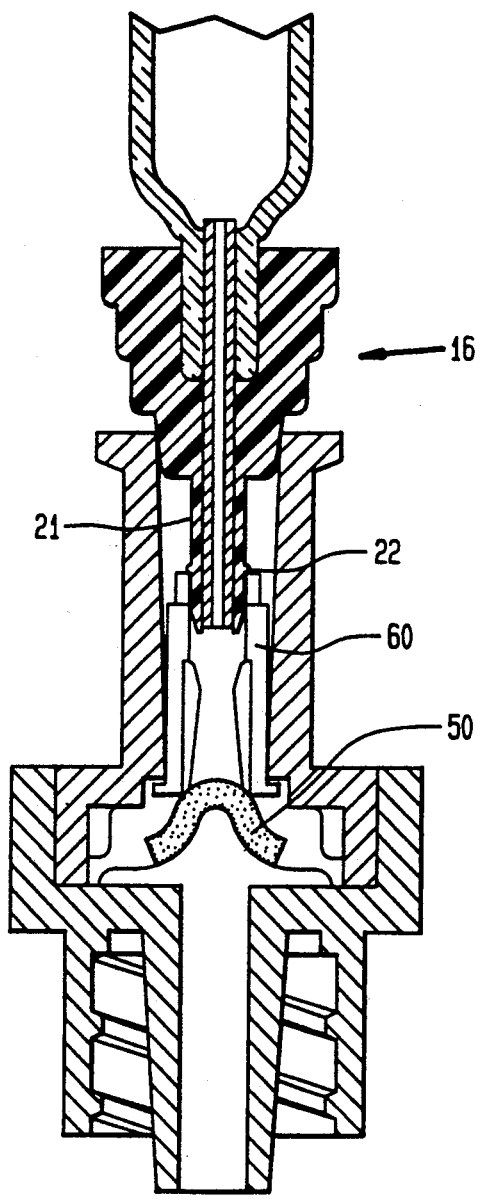

It should be understood that the annular projection 22 need not be continuous about the circumference of the forward extension 21 but may appear as two or more discontinuous protrusions of the same size as the ring, which function in the same manner as a continuous ring when brought to bear on valve member 60 as shown in FIGS. 2 and 3. As such, when reference is made to an annular projection in this disclosure, it is intended to embrace two or more projections disposed in the same site of the forward extension as ring 22 and functioning in the same manner as ring 22 in conjunction with the modified Luer stub 20 in an injection port as shown in FIGS. 2 and 3.

In use, the needleless syringe of this invention is inserted into an intravenous injection port as shown in FIG. 2 where the annular projection 22 about the circumference of the forward extension 21 of the syringe hub 16 engages the member 60 and with the application of force moves 60 inward thereby opening valve disk 50 and seating the modified Luer slip fitting 20 of the syringe in the female Luer slip fitting of the injection port. After administration of the intravenous solution, withdrawal of the needleless syringe permits return of the valve disk 50 to its original closed position as shown in FIG. 2. The needleless syringe of this invention is then discarded. No danger of infection or medication transfer to the medical personnel operator is involved in this operation.

What is claimed is:

1. A needleless syringe comprising a barrel consisting of a tube with a constricted distal end region, a plunger disposed within the barrel and a fluid transfer tube extending into and secured to the constricted distal end of said barrel by an externally stepped hub connector through which said fluid transfer tube partially extends, said externally stepped hub connector comprising (1) a tubular skirt section of greatest circumference secured to the constricted distal end of said barrel through which said fluid transfer tube extends; (2) a tubular male tapered section of smaller circumference situated distal to the constricted distal end of said barrel and through which said fluid transfer tube extends; and (3) a tubular extension of smallest circumference extending distally from said male tapered section to a terminal aperture for fluid discharge, said fluid transfer tube projecting into said tubular extension of smallest circumference to an internal point near said aperture for fluid discharge, said tubular extension having an annular ring projection about its circumference at a distance distal to said tapered section sufficient to create a seal between said tapered section and a female luer slip fitting of a valve-actuated intravenous port device when said annular ring projection opens said valve, said annular ring projection having a circumference smaller than the smallest circumference of said tapered section.

2. A needleless syringe as defined in claim 1 in which said hub connector is formed from nylon.

3. A syringe as defined in claim 1 in which said tubular male tapered section comprises a modified Luer slip capable of forming an air-liquid tight connection with a female Luer slip.

4. A syringe as defined in claim 3 in which said modified Luer slip of said hub connector is from about 0.172 to 0.180 inches in diameter at its large end and about 0.167 to about 0.159 inches at its smallest end over a length of from about 0.250 to about 0.120 inches.

5. A syringe as defined in claim 1 in which said barrel is pre-filled with a standard intravenous medication.

* * * * *